United States Patent [19]

Matson et al.

[11] E Patent Number: Re. 32,920

[45] Reissued Date of Patent: May 9, 1989

[54] ELECTROCHEMICAL TESTING SYSTEM AND METHOD

[75] Inventors: Wayne R. Matson, Ayer; Ronald Vitukevich, Everett, both of Mass.

[73] Assignee: ESA, Inc., Bedford, Mass.

[21] Appl. No.: 426,690

[22] Filed: Sep. 29, 1982

Related U.S. Patent Documents

Reissue of:

[64] Patent No.: 4,233,031
Issued: Nov. 11, 1980
Appl. No.: 968,060
Filed: Dec. 11, 1978

U.S. Applications:

[63] Continuation-in-part of Ser. No. 868,654, Jan. 11, 1978, abandoned.

[51] Int. Cl.[4] ..... G01N 27/46

[52] U.S. Cl. ..... 204/1 T; 204/400; 204/409; 204/411; 204/412; 422/68; 422/98; 436/151

[58] Field of Search ..... 204/400, 409, 412, 411; 422/68

[56] References Cited

U.S. PATENT DOCUMENTS

| | | | |
|---|---|---|---|
| 2,773,020 | 12/1956 | Offutt et al. | 204/413 |
| 3,051,631 | 8/1962 | Harbin et al. | 204/400 |
| 3,208,926 | 9/1965 | Eckfeldt | 204/409 |
| 3,298,934 | 1/1967 | Angeleri | 204/1 T |
| 3,301,775 | 1/1967 | Tsien | 204/412 |
| 3,413,199 | 11/1968 | Morrow | 204/269 |
| 3,504,323 | 3/1970 | Meany | 204/404 |
| 3,539,455 | 11/1970 | Clark | 204/412 |
| 3,551,109 | 12/1970 | Dahms | 23/230 |
| 3,556,950 | 1/1971 | Dahms | 204/1 T |
| 3,563,875 | 2/1971 | Coulson | 204/405 |
| 3,629,089 | 12/1971 | Luck | 204/412 |
| 3,648,159 | 3/1972 | Stansell et al. | 23/230 B |
| 3,709,985 | 1/1973 | Burke | 23/230 BR X |
| 3,874,850 | 1/1975 | Sorensen et al. | 23/230 |
| 3,887,332 | 1/1975 | Takase et al. | 23/230 B |
| 3,918,910 | 11/1975 | Soya et al. | 23/253 R |
| 3,923,627 | 12/1975 | Niedrach et al. | 204/195 R |
| 4,090,926 | 5/1978 | Matson | 204/413 |

FOREIGN PATENT DOCUMENTS

| | | | |
|---|---|---|---|
| 1372245 | 10/1974 | United Kingdom | 27/7 |
| 1460892 | 1/1977 | United Kingdom | 27/7 |
| 1465417 | 2/1977 | United Kingdom | 27/7 |

OTHER PUBLICATIONS

Kissinger et al., *Anal. Lett.*, 6(5), (1973), pp. 465–477.

Blank, "J. of Chromatography", 117 (1976), pp. 35–46.

Gerischer et al., "J. Electroanal. Chem.", vol. 10, (1965), pp. 553–567.

A Dual Working Electrode Coulometric Flow Cell, by John V. Kenkel and Allen J. Bard, Electroanalytical Chemistry and Interfacial Electrochemistry 54 (1974), pp. 47 to 54.

*Primary Examiner*—T. Tung

*Attorney, Agent, or Firm*—Hayes, Davis & Soloway

[57] ABSTRACT

An electrochemical measuring system which effects, measures and sorts charge transfer reactions of selected substances in a sample solution is provided. The system includes a novel electrode which is adapted to measure simultaneously on at least two electrodes at least two electrolytic potentials with reference to a reference potential. In a preferred form the electrode comprises a hollow, cylindrical body formed of an electrically insulating material. The electrode is open at least at one end and has a generally smooth cylindrical inner surface. A plurality of electrically discrete active electrode segments are mounted on the inner surface of the electrode with their active surfaces substantially flush with the generally smooth cylindrical inner surface. Completing the electrochemical measuring system are a stirring means for creating a relatively high degree of mixing adjacent the electrode active surfaces, means for charging liquid samples to the cell, and means connecting at least two of the electrically discrete active electrode segments to different electrical potentials. In use a sample to be tested is charged to the cell, and stirring is commenced. One of the electrically discrete active electrode segments is held at a potential at which a selected substance of interest and also one or more interferring substances responds, while another of the electrode segments is held at a potential at which only the interferring substances respond. The presence of a substance of interest can be determined by subtracting the signals from the one and another electrode segments, and its quantity determined by integrating the signal difference.

28 Claims, 4 Drawing Sheets

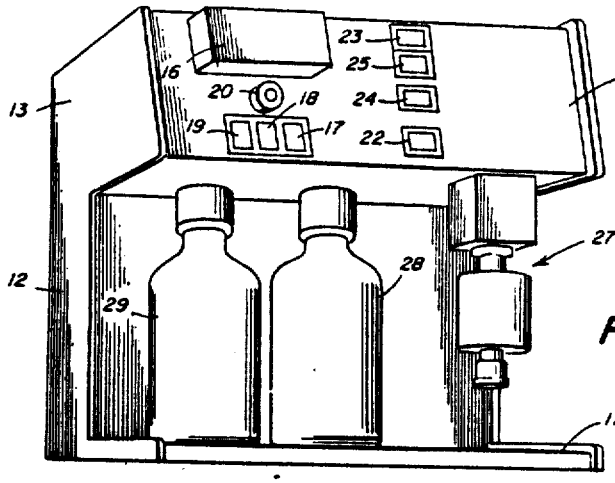
FIG. 1
FIG. 3
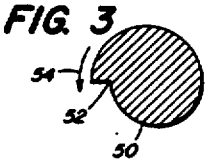
FIG. 4
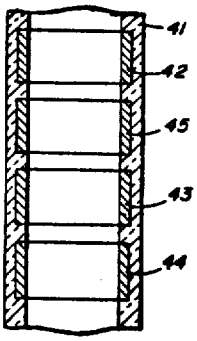
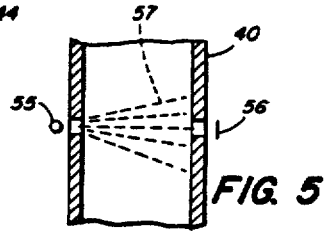
FIG. 5
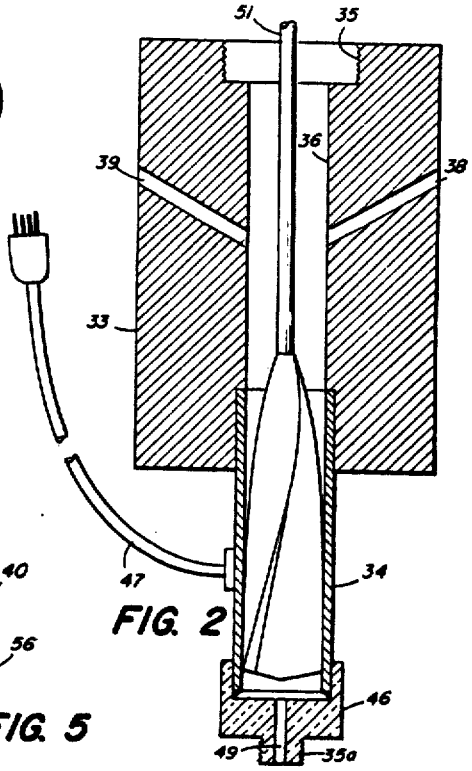
FIG. 2

GRAPHITE STIR ROD 51A
REAGENT OUTLET
SAMPLE INLET

52C
TEST ELECTRODE
REF. ELECTRODE
TEST ELECTRODE
50C
ELECTRODE CELL 27C
CTR ELECTRODE
CELL END CAP
TEST ELECTRODE
REF. ELECTRODE
50D
ELECTRODE CELL 27D
TEST ELECTRODE
CTR ELECTRODE
CELL END CAP
52D
REAGENT INLET

ELECTROCHEMICAL TESTING SYSTEM AND METHOD

Matter enclosed in heavy brackets [ ] appears in the original patent but forms no part of this reissue specification; matter printed in italics indicates the additions made by reissue.

The present application is a continuation-in-part of our copending application Ser. No. 868,654, filed Jan. 11, 1978 now abandoned.

Various electrochemical systems are known in the art for detecting the presence of and/or measuring the concentration of various substances of interest in sample solutions suspected of containing the selected substances, and find utility in a variety of environmental, medical and industrial applications. Generally, such systems are employed in analyzing for metallic ions of interest, although systems also exist for the detection of non-metals such as cyanide ion, sulfur dioxide and halogen, and for certain organic materials.

One type of prior art electrochemical analysis employs gravimetric methods in which a deposit formed by electrical action is weighed on an analytical balance. Gravimetric methods are prone to weighing errors, require a skilled technician, and are relatively time consuming and insensitive.

Another type of prior art electrochemical analysis employs ion-selective electrodes. A number of ion-selective electrodes have been devised for testing for a variety of ions of interest and are considered to be reliable and relatively easy to use. However, a number of substances of interest in the environmental industrial and medical fields cannot be measured with ion selective electrodes. Moreover, ion-selective electrodes respond logarithmically and thus generally are not sufficiently sensitive for measuring concentrations below about $10^{-5}$ to $10^{-6}$ molar.

Polarographic analysis based on current voltage curves obtained with hanging drop mercury electrodes offers an advantage over ion-selective electrodes of sensitivity in dilute solutions. A feature and requirement of classic hanging drop mercury polarographic electrolysis cells is the dropping mercury electrode, i.e., mercury droplets being discharged periodically into a solution from a fine bore capillary under a driving head of mercury. However, this very feature, which has permitted the initiation of extremely useful polarographic methods in research work, mitigates against a more general use of classic polarographic electrolysis cells as common analytical systems, and in particular as tools for monitoring and controlling industrial process streams or for field use testing in medical and environmental applications. Moreover, the characteristic periodic growth and fall of the mercury droplets cause oscillations in the current-voltage curves obtained using such cells and thus prevent the establishment of standard curves. Other problems of hanging drop mercury electrodes which have essentially limited cells employing same to laboratory and experimental use include condensor current build-up whenever a new mercury droplet is being formed at the capillary, and limited surface area of the droplets which limits sensitivity of the electrode. In addition, formation of the tiny mercury droplets is a delicate process which may be affected by a number of incidental factors, including mechanical vibration, slant of capillary, and pulsation of test solutions into the capillary inlet between drops. In this connection it should be noted that the reproducibility of droplets with regard to their drop line and mass of mercury per drop must be practically perfect at all times to permit proper evaluation of the polarogram.

Still another type of prior art electrochemical measuring system is a technique called coulometric shipping voltammetry. Coulometric stripping voltammetry is a two-step process comprising electrodepositing the electroactive material of interest on or in an indicating or working electrode and then electrodissolving or stripping the deposited material back into solution. In anodic stripping voltammetry, the material to be measured is plated onto an electrode by applying a negative potential over an extended time period, and then stripping the material off the electrode over a relatively short period by sweeping to a positive potential. The order of potential at which the elements of the material are stripped off the electrode provides a qualitative analysis of the material, and the quantity of the current provides a quantitative analysis. Anodic stripping voltammetry offers the advantages of enhanced sensitivity, resolution, and reproducibility compared to classical polarographic analysis obtained using hanging drop mercury electrodes. By way of example, thin-film mercury/-graphite composite electrodes have been employed in anodic stripping voltammetry systems for analyzing for metals at the sub-nanogram level. See, for example, the reported work of Wayne R. Matson, Reginald M. Griffin, and George B. Schreiber in "Rapid Sub-Nanogram Simultaneous Analysis of Zn, Cd, Pb, Cu, Bi and Ti", Trace Substances in Environmental Health, University of Missouri, Dr. D. Hemphill, Ed; pp. 396–406, (1971). While electrochemically analyzing solutions employing composite mercury/graphite electrodes by anodic stripping voltammetry, e.g. as taught by Matson et al, supra, may provide sub-nanogram sensitivity, the ability to rapidly and reliably differentiate and measure selected substances at the picogram level is not generally possible using existing electrochemical measuring techniques. Also, many metals interact with the electrode to form an alloy of analgam. Thus, anodic and cathodic stripping voltammetry are limited to detection of a relatively small number of species of metals and non-metals. Obviously, the ability to operate at such low concentrations and on a wider variety of species would have major commercial utility in environmental, medical and industrial applications.

It is thus a primary object of the present invention to provide a novel and improved system, i.e. method and apparatus, which overcomes the aforesaid and other problems and limitations of the prior art.

Another primary object is to provide a novel and improved method and apparatus for electrochemically analyzing a sample in order to qualitatively and/or quantitatively determine the presence of selected substances in the sample.

Another object of the present invention is to provide an electrochemical measuring system of the aforesaid type which is capable of rapidly and reliably operating at the picogram level of sensitivity.

A more specific object is to provide a novel and improved electrode for use in electrochemical systems.

In order to effect the foregoing and other objects there is provided an electrochemical measuring system which effects, measures and sorts charge transfer reactions of selected substances in a sample solution. The system includes a novel electrode which is adapted to measure simultaneously on at least two electrodes at two electrolytic potentials with reference to a reference potential. In a preferred form the electrode comprises a hollow, cylindrical body formed of an electrically insulating material. The electrode is open at least at one end and has a generally smooth cylindrical inner surface. A plurality of electrically discrete active electrode segments are mounted on the inner surface of the electrode with their active surfaces substantially flush with the generally smooth cylindrical inner surface. Completing the electrochemical measuring system are a stirring means for creating a relatively high degree of mixing adjacent the electrode active surfaces, means for charging liquid samples to the cell, and means connecting at least two of the electrically discrete active electrode segments to different electrical potentials. In use a sample to be tested is charged to the cell, and stirring is commenced. One of the electrically discrete active electrode segments is held at a potential at which a selected substance of interest and also one or more interferring substances responds, while another of the electrode segments is held at a potential at which only the interferring substances respond. The presence of a substance of interest can be determined by subtracting the signals from the one and another electrode segments, and its quantity determined by integrating the signal difference.

Yet other objects of the invention will in part appear obvious and will in part appear hereinafter. The invention accordingly comprises the apparatus possessing the construction, combination of elements, and arrangement of parts, and the process comprising the several steps and the relation of one or more of such steps with respect to each of the others, all of which are exemplified in the following detailed description, and the scope of the application as will be indicated in the claims.

For a fuller understanding of the nature and objects of the present invention, reference should be had to the following detailed description taken in connection with the accompanying drawings wherein:

FIG. 1 is a front view in perspective of a preferred form of electrochemical measuring apparatus according to the invention;

FIG. 2 is a front view, partially in section, or a preferred form of electrolytic cell of the apparatus of FIG. 1;

FIG. 3 is an end view, in cross-section of the sample solution stirring member of apparatus of FIG. 1;

FIG. 4 is a fragmentary plan view, in cross-section of a preferred form of sensing electrode element of the apparatus of FIG. 1;

FIG. 5 is a diagrammatic view of a flow detector element of the apparatus of FIG. 1;

Figure 6:
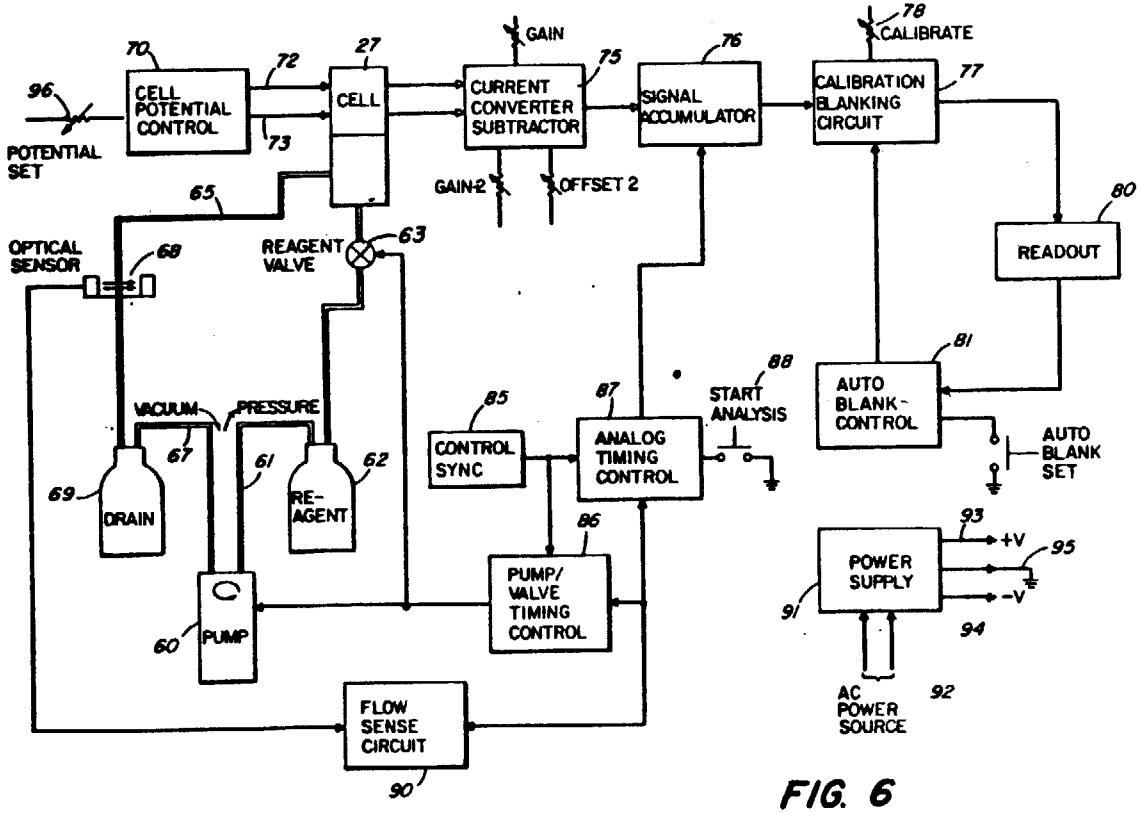
FIG. 6 is a block diagram of the electrical and pneumatic controls and functions of the apparatus of FIG. 1.

The present invention is based on measurements of electrochemical reactions of selected substances in solution under controlled potential conditions. As is well known in the art, when electroactive substances are dissolved in a solvent to form a reagent of electrolyte, and an electrical current passed through the electrolyte between an anode and a cathode disposed therein, positive ions will be attracted to the negatively charged cathode where their charge will be neutralized, while negative ions will move towards and be discharged at the anode. The electrical potentials at which such electrochemical reactions occur will vary depending upon the particular substances involved. By way of example, consider an aqueous solution which contains both iron and copper ions. Iron normally exhibits a valence of two or three, while copper normally exhibits a valance of one or two. The electrical potential at which ferric ions ($Fe^{+3}$) in solution may be reduced to ferrous ions ($Fe^{+2}$) is a constant at a given temperature. Likewise, the electrical potential at which cupric ions ($Cu^{+2}$) in solution may be reduced to cuprous ions ($Cu^{+1}$) is also a constant at a given temperature, and is different from the electrical potential at which the reduction of ferric ions to ferrous ions occurs. (The electrical potential at which such reactions occur are approximately described by tables of standard or formal potentials). The absolute value of the electrical potential of ions of solution is indeterminate. However, electrochemical reactions for a particular species are described in terms of a potential versus a standard reference couple such as $H_2H^+$. The magnitude of the potential is a measure of the potential that has to be applied versus a standard reference electrode to force charge transfer to occur. The electrical potential at which such reactions will occur is referred to as the "Charge transfer potential".

Assigning an arbitrary value of zero to hydrogen, the potential E of an electrochemical reaction may thus be written according to the following reaction:

$$E = E_o - \frac{0.05915}{n} \log_{10} \frac{(A_p)^x}{(A_R)^y} \quad (1)$$

where n is the number of Faradays, $A_P$ and $A_R$ are activities of the product reactants, and x and y are corresponding coefficients of the electrochemical reactions. Thus, the potential $E_o$ is the standard potential related to the particular reaction. E is a potential applied to drive the reaction either to reactants or products according to the equilibrium condition described by equation (1). Under conditions where the E applied is large enough to drive the reaction to virtual completion at equilibrium, the current derived will be proportional to the concentration of the reactant in the solution. However, background noise prevents direct measurement of most sample solutions and in the case of very dilute solutions may prevent direct measurement in many instances. (As used herein the term "background noise" is intended to refer both to major interference factors such as the presence in the solution of other electroactive materials which, by virtue of their electrical activity in the solution, respond to the same electrical potential as the ion of interest, and also major non-Faradaic interference factors such as capacitance signals of the electrode in the solution due to the existence of a boundary layer of still solution adjacent the active surfaces of the electrode, bulk solution signals, inherent Faradaic signals, electrode settling signals and the like). A feature and advantage of the present invention resides in the elimination of and/or cancellation of background noise through a combination of electrochemical manipulations and electrode geometry.

Further understanding of the features and advantages of the present invention will be had from the following detailed description of one preferred embodiment of the invention which illustrates an electrochemical testing system for measuring the iron content in serum or blood. It will be understood however, that the system of the present invention may be advantageously employed for detecting the presence of and measuring the concentration of various other substances of interest in sample solution.

Referring to FIG. 1, there is illustrated an electrochemical measuring apparatus indicated generally at 10 including a base 11. Mounted on base 11 by means of upright support 12 is a cabinet 13 whose front face acts as a control panel 14. Mounted on the panel are various control means including a a display panel 16, function buttons including a standby button 17, an "autoblank" control button 18, an "autoblank set" button 19, and a calibration knob 20. Also positioned on the control panel 14 is an off-on button 22, a flow indicator 23 suitably labelled to show that a prior sample is flushed out and a new test may be started. Also on the control panel are a start button 24, and a "running" indicator 25. For convenience it is preferred that the controls be combinations of push-buttons and indicating lights, and in the actual apparatus such combination buttons and lights are used.

Depending from the bottom of cabinet 13 is a cell assembly 27 indicated in outline and shown in further detail in FIG. 2. Positioned on base 11 are two containers 28 and 29, suitably connected by plastic tubing or the like to the cell block. Container 28 receives flushed cell contents at the end of each run and container 29 holds a supply of fresh cell liquid or electrolyte.

FIG. 2 shows the cell assembly of the apparatus of FIG. 1 comprising generally a cell block 33 and a sensing electrode 34 mounted therein. Cell block 33 comprises a suitable mounting piece such as, for example, a plastic block having a screw threads 35 or other mounting means at the upper end. A vertical channel or cylindrical hollow 36 runs through the cell block and communicates with the interior of sensing electrode 34. Two passageways, the first an inlet passage 38 to receive a sample to be tested which may, for example, be by means of a pipette (not shown) inserted into channel 38, and the second an outlet passageway 39 for cell liquid. Cell block 33 is formed of a liquid-impervious, rigid, electrically insulating, chemically inert material such as unplasticised polyvinyl chloride, polytetrafluoroethylene fluorocarbon resins or the like.

The bottom of channel 36 is recessed to receive sensing electrode 34. Sensing electrode 34 is in the form of a hollow cylinder, and the inner surface of the electrode and the inner surface of channel 36 are flush and as smooth as possible so as to minimize the material caught therebetween. In actual practice the electrode is permanently mounted in the cell block by suitable means such as, for example, by an epoxy resin or the like, and the inner surface of the joint between the two is machined smooth.

At the bottom of sensing electrode 34 is a seal and connector device 46 which may, for example, be in the form of a plastic plug molded to the sensing electrode 34 having a screw thread connection 35a for connecting a pipe or hose thereto and having a channel 49 extending therethrough. A continuous passage is thus formed, and electrolyte or other contents of the cell can be flushed out by passing fresh electrolyte or other liquid in through channel 40 and out through outlet 39 in the cell block above the electrode.

As mentioned supra an important feature and advantage of the present invention is the ability to differentiate between electrical signals representative of the charge transfer electrolytic reaction of selected substances of interest, and electrical signals derived from the bulk sample solution, interferring substances and other background noise. This feature and advantage is made possible in part by the construction of sensing electrode 34. Sensing electrode 34 comprises a generally cylindrical body of block epoxy having mounted therein a plurality of active electrode segments. The electrode body comprises an electrically insulating material such as a polymeric material while the active electrode segments comprise a suitable electrode base such as graphite, pyrolytic graphite or platinum, or the active electrode segments may comprise coatings of active electrode material such as mercury or gold. In practice, at least two electrically discrete electrode areas are employed, for example, in the form of rings or bands of active electrode surface on the inside of a hollow electrode body. The segments are separated by electrically insulating bands on the inside of the electrode. Such an electrode can be formed by holding segments of active electrode material in the form of rings in desired position and molding the rings with an electrically insulating such as an epoxy resin to form a cylinder. Sensing electrode 34 is shown in further detail in FIG. 4. For convenience of illustration sensing electrode 34 has been shown as comprising two active testing electrode segments, a counter or power supplying electrode segment, and a reference electrode segment as follows:—a first active testing electrode segment 42, a second active testing electrode segment 43, a third counter electrode segment 44, and a reference electrode segment 45. The first, second and third active electrode segments 42, 43 and 44 are formed of suitable electrode material such as graphite or the like while the reference electrode segment 45 is formed of silver, palladium or the like. Electrode segments 42, 43, 44 and 45 each comprise a cylindrical ring embedded into a cylindrical electrode body 41. The electrode segments are spaced apart by a narrow gap so as to be electrically insulated one from the other, and the electrode segments are mounted so that the active surfaces are substantially flush with the inner surface of electrode body 41 so that the inner surface of the entire electrode 34 is a smooth as possible. Electrical connections (not shown in FIG. 4) are provided to each of the electrode segments and are suitably connected to the apparatus by means of a four wire lead terminating in a four-pronged plug as shown in FIG. 2. Obviously the electrode may comprise additional active electrode segments.

Positioned within electrode 34 is a stirring means 50. Stirring means 50 is mounted for rotation within the electrode body by means of rod 51. Stirring means 50 and rod 51 are formed of electrically insulating and chemically inert materials such as molded resin. The lower end of stirring means 50 is slightly wedge-shaped or cone-shaped, and is generally close fitting within the electrode body. A diagonal groove 52 which is better seen in FIG. 3 runs along the surface of the stirring means 50. When rotated in the direction shown by arrow 54, groove 52 creates a high degree of mixing or turbulence closely adjacent to the active surfaces of electrode segments 42, 43, 44 and 45 so as to minimize the thickness of the boundary layer of still solution adjacent the active surfaces of the electrode segments, while maximizing mass transfer to the electrode surfaces.

In use off-on button 22 is first activated. Ordinarily, the apparatus will be left running in a standby condition overnight and will be turned off if it is to be left idle for a period of a week or more. At the start of each week, or for purposes of abundant caution at the start of each day, the apparatus may be calibrated. It is first operated with the calibration button in operating position to standardize the electronics as will be hereinafter described. A blank sample of reagent is run first. Then the "auto-blank" button 19 is set, holding the calibration. Next a standard sample of known ion concentration is introduced into the cell 27 and the apparatus run through a cycle. When it has been properly standardized, the calibration knob 20 is adjusted so that the reading in the display panel 16 corresponds with the known ion quantity in the standard calibration sample.

A plastic tube or pipe 40 (not shown in FIG. 2) connects the cell assembly 27 to the apparatus. At a selected point along tube 40 and preferably within cabinet 13 is a flow detector illustrated diagrammatically in FIG. 5. An emitter 55 or other light source is positioned near a window at a point along tube 40. The window may be a transparent insert or the tube itself may be transparent. Opposite emitter 55, i.e. on the opposite side of the tube 40 is a detector 56 positioned adjacent a similar window. When tube 40 is empty or filled with a gas the beam of light 57 from the emitter is quite diffuse. When tube 40 is filled with a liquid such as the cell electrolyte flowing through the tube, the liquid acts as a lens and increases the sharpness of focus of light beam 57. Detector 56 is adjusted for a threshold such that it can determine the presence of liquid in tube 40 and the length of time such liquid is present. The signal from detector 56 is employed to indicate that there has been flow of liquid through tube 40 for a sufficient time to accomplish flushing out of cell electrolyte after a single run so as to remove the sample therefrom.

In repetitive runs the cell 27 is repeatedly filled with an electrolyte and the cell stirring apparatus is constantly in operation to keep the cell contents uniform and mixed. A known quantity of a test sample is then pipetted into a cell 27. The running indicator 25 lights to show that the test is in operation. In a preferred embodiment of the present invention the display panel is a digital display which counts to zero and then up to the number of micrograms per 100 milliliters of serum (μg %). When the digital display stops counting the test is complete. After a timed waiting period the cell electrolyte containing the sample is flushed into container 28 and a new supply of electrolyte is introduced into the cell from container 29. When the start test indicator 24 lights up again, the apparatus is ready for a next sample.

In FIG. 6 is shown a block diagram of electrical and fluid flow controls for the foregoing apparatus. A cell 27 such as the cell of FIG. 1 is connected to have a reagent or electrolyte conveyed therethrough is individual analysis quantities. A pump 60 pumps air through a line 61 from a reagent container 62. A reagent valve 63 controls flow of the reagent to cell 27. Referring to FIG. 2, the reagent flows into lower channel 49 and thus into and through the cell 27. Another fluid line 65 is positioned to carry the reagent or other liquid from the cell 27 past an optical sensor 68 such as, for example, the sensor shown in FIG. 5. Line 65 then conveys the liquid to a drain container 69. A vacuum line 70 returns to pump 60. Thus the flow of the liquid through cell 27 is into the bottom of the cell and out through outlet 39 positioned above the cell. Preferably inlet channel 38 in cell 27 will be located slightly above outlet channel 39 so that liquid normally will flow out channel 39 rather than channel 38.

For analyzing a sample the sample is dissolved in a solvent to form an electrolyte or reagent. By way of example, for testing for iron in blood or serum a small sample of blood or serum, typically a 5 to 100 microliter sample is added to an electrolyte or chemical reagent which releases iron from its serum bonding and separates the transfer potentials of iron and its most usual interferring element, copper.

If total iron-binding capacity is being measured, the serum is first fully saturated with iron, as by mixing it with an iron-containing ion exchange resin.

Preferably, the electrolyte or reagent for treating serum to release iron for testing comprises strong hydrochloric acid, e.g. between about 5½ and about 8½ Formal, and preferably about 7 Formal, in a lower alcohol such as propanol or isopropanol. Methanol and ethanol have been found nearly as effective as propanol or isopropanol, but have the disadvantage that they are more expensive, and they are more volatile and therefore more difficult to handle. Higher alcohols such as butanol and the like are operable, but are less compatible with strong hydrochloric acid. Other materials such as acetonitrile and acetone are also operable but are less satisfactory partly because of less satisfactory performance and partly because of cost, volatility, toxicity and the like. The apparatus is calibrated in accordance with the selected strengths of the hydrochloric acid.

The use of strong hydrochloric acid in lower alcohol as an electrolyte or reagent to release iron from its serum bonding and to separate the transfer potential of iron and its most usual interferring substance, i.e. copper, in order to prepare the blood or serum for electromechanical analysis for iron is believed novel.

In place of hydrochloric acid there may be employed other compounds having a high chlorine or halogen content, but such other compounds have not been found to be fully satisfactory. For example, lithium chloride is a more expensive source of chloride iron and also tends to precipitate at least a portion of the serum. Hydrogen bromide is another source of halogen ion but is also more expensive and is notably more difficult to work with and is corrosive.

Included in the reagent or electrolyte is an extremely minute quantity of silver ion in the range of about 200 parts per million which assists in the operation of the silver reference electrode segment 45. The reference potential is the silver ion potential, maintained by reference electrode segment 45. Accordingly, the reagent or electrolyte preferably will include 7 Formal HCl in propanol together with 200 parts per million silver ion and such reagent or electrolyte will release iron from serum or its iron binding components to make the iron available to electromechanical measurement and also will permit separation of the charge transfer potentials of iron and copper, and give reproducible results in the analysis of serum iron by electrochemical measurement techniques in microliter sample quantities.

The prepared sample comprising a serum to be tested, together with a measured quantity of a reagent or electrolyte is charged to cell assembly 27, and stirring commenced.

A potential control 70 applies two different electrical potentials 72 and 73 to two of the active testing electrode segments, e.g. electrode segments 42 and 43. Electrical potential 72 is set at a value which causes an electrochemical reaction of both iron and copper, while electrical potential 73 is set at a value which causes electrochemical reaction of copper alone, as will be described in detail hereinafter. A reference potential is applied to the silver electrode segment 45, and another potential is applied to counter electrode segment 44 and provides a source of current to the cell. Alternatively counter electrode segment 44 may be held at ground. The current or signals from first and second testing electrode segments 42 and 43 are fed to a logic module which subtracts the first signal from the second and, if desired, applies a multiple for calibration purposes. By way of example, the current or signals from the two active electrodes segements in the cell 27 can be fed to a current convertor subtractor 75 with two variable gains for adjustment. The signal then goes to a signal accumulator 76, and then to a calibration blanking circuit 77 which also has a variable gain or calibrator 78. The signal from the calibration blanking circuit 77 then is fed to a readout 80 and, in turn, to an autoblank control 81. The signal from the autoblank control is returned to the calibration blanking circuit 77. When the calibration is correct, an autoblank set 82 is operable to fix the circuits.

The electrochemical reactions which take place and are measured by the apparatus are the reduction of ferric ion to ferrous ion, the oxidation of ferrous ion to ferric ion, and the reduction of cupric ion to cuprous ion. (Generally, material will not be deposited on the active electrode segments, and accordingly these reactions may be considered to be "charge transfer" rather than electrolytic or electrodeposition reactions). At active electrode segment 42 there occurs the reduction of ferric ion ($Fe^{+3}$) to ferrous ion ($Fe^{+2}$) and the reduction of cupric ion ($Cu^{+2}$) to cuprous ion ($Cu^{+1}$). At active electrode segment 43 there occurs the reduction of cupric ion to cuprous ion and the oxidation of ferrous ion to ferric ion. As a matter of choice, active electrode segment 42 is set at the higher potential. The signal at the one electrode is subtracted from the other with the following result:

$$\text{(A) } Fe^{+3}+e^{-}\rightarrow Fe^{+2};\ Cu^{+2}+e^{-}\rightarrow Cu^{+1} \text{ and} \quad (2)$$

$$\text{(B) } Fe^{+2}\rightarrow Fe^{+3}+e;\ Cu^{+2}\rightarrow Cu^{+1}-e. \quad (3)$$

by subtraction $$\text{(A)}-\text{(b)}=Fe^{+3} \text{ and } Fe^{+2};\ Cu\rightarrow 0. \quad (4)$$

As can be seen, the reduction of cupric to cuprous ion is cancelled out in the logic with the result that the total of iron content is the signal which is fed to the digital or other readout.

Generally, the potential on active electrode segment 42 may be varied between about 0 to 1 volt while the potential on active electrode segment 43 may be varied between about 0 to 300 millivolts from that of segment 42. For testing the serum iron in accordance with the foregoing technique active electrode segment 42 will be set at a potential of about 460 millivolts while active electrode segment 43 will be set at a potential of about 250 millivolts.

It is to be appreciated that the invention is not limited to the measurement of serum iron, but that any electroactive substance may be detected and measured using the foregoing process and apparatus. By way of example, the electrochemical measuring system of the present invention may be used for detecting and measuring heavy metals such as zinc, cadmium, lead, copper, bismuth, gold, silver and thallium in blood samples. As is well known in the art such heavy metals normally are complexed with blood, and thus must be released before than can be measured. A number of reagents are known in the art and are available commercially for releasing such heavy metals from human blood. One such reagent is called METEXCHANGE® and is available from Environmental Sciences Associates, Inc., of Bedford, Mass. The manufacturer describes this reagent as comprising a dilute aqueous solution of calcium chloride, chromium tri-chloride, hydrogen ion, phosphate ion, acetate ion and a dispersing agent. The mixture of calcium ion and chromium ion is said to cause release of complexed heavy metal in blood so that the total concentration of heavy metal can be effectively measured.

Moreover, the invention is not limited to the detection and measurement of heavy metals in biological samples. For example, heavy metals complexed with gasoline can be detected and measured in accordance with the foregoing by dissolving gasoline samples in a reagent which comprises a dilute mixture of ICl, NaCl, $N_2H_4HCl$ and a polyalcohol. The same reagent can be used to release various other heavy metals from a wide variety of organic samples. Other reagents which contain a metal ion which will displace the heavy metal of interest from the complex can also be used.

Additionally, a large number of organic substances are electroactive and thus can also be detected and measured in accordance with the foregoing invention including: unsaturated hydrocarbons, azides, triazines and phenothiazines, amino acids, amines and amides, phenols, aromatic OH, quinolines, quinones, imines, olefins, ketones, aldehydes, esters, and olefinic esters, ethers, organometallics, diazo compounds, nitro compounds, and halogens. The same reagents which are useful for dissolving these organic substances for liquid chromatography generally can also be used as the reagent in the process of the present invention. Amongst suitable reagents are mentioned: water, lower alcohols, such as methanol, ethanol and isopropanol, and mixtures thereof. If required a strong inorganic acid such as hydrochloric acid or phosphoric acid, a strong base such as sodium hydroxide, or a salt such as sodium chloride may be included in the reagent to release the species of interest from a complex. For example, for analyzing blood samples for the presence of Tylenol, morphine or heroin in accordance with the present invention a suitable reagent comprises methanol/water/phosphoric acid mixture comprising about 30% methanol, 0.1 to 1% phosphoric acid, and the balance water. For analyzing blood samples for essential trace elements such as zinc, an aqueous solution of calcium acetate buffered to pH 3 has been found to be a suitable reagent. A normal saline reagent may be used to measure glucose in blood or serum.

The electrochemical measuring system of the present invention may also be advantageously employed for detecting and measuring substances such as cyanide, halogen, $SO_2$ and $NO_x$ in biological samples, water or sewage. The electrochemical measuring system of the present invention may also be adapted for use in monitoring of electroactive substances in chemical process streams. The required electrode potentials are approximately the same as would be employed in controlled potential coulometric stripping of the same organic substances.

The extreme sensitivity of the electrochemical measuring system of the present invention permits accurate measurements in picogram region. Thus, the electrochemical measuring system of the present invention may be advantageously employed for making soil analysis for agricultural purposes and may also be used for metal prospecting. In regard to this latter feature, the process involves measuring soil and/or water samples taken in a grid pattern in order to zero in on significant deposits of selected metals. By way of example, to zero in on deposits of relatively rare metals such as molybdenum, tungsten, vanadium, titanium and uranium soil or water samples taken on a grid are extracted with and analyzed in a reagent comprising alcoholic HCl solution such as a 20% solution of methanol in HCl. The electrolyte is then charged to the cell, one of the active electrode segments is set at an electrical potential to oxidize the metal of interest while another of the active electrode segments is set at an electrolytic potential to oxidize the metal of interest plus other interferring metals. The required electrode potentials are approximately the same as would be employed in controlled potential coulometric analysis of the same metal or metals. Other metals may be measured by changing the electrode potentials and/or the reagent. For example, for chromium a preferred reagent is alcoholic hydroxide solution such as 0.8 normal NaOH in methanol. The use of an alcoholic HCl solution as reagent for electrochemical analysis of molybdenum, tungsten, vanadium, titanium and uranium, and the use of an alcoholic hydroxide solution as reagent for electrochemical analysis of chromium are believed novel.

Gaseous samples and/or airborne samples can also be analyzed by bubbling the gas or air through a suitable reagent to dissolve the substance of interest. The electrolyte can then be charged to the electromechanical cell as above described, and measurements made in accordance with the foregoing.

One skilled in the art will recognize that the invention is susceptible to modification. Thus, sensing electrode 34 in accordance with the present invention has been shown as comparing two active testing electrode segments, a reference electrode segment and a counter electrode segment with the electrical potentials on the two active testing electrode segments being adjusted according to the particular substances being detected and measured. One skilled in the art will recognize, however, that electrode 34 may comprise a large number of active testing electrode segments, e.g. electrode 34 may comprise 50 or 100 electrically discrete active testing electrode segments, each segment being electrically connected to a different electrical potential to effectively reproduce an entire current voltage curve. For example, the electrode 34 may comprise twelve active testing electrode segments at a series of electrical potentials, which may be 20 to 80 millivolts offset. Thus, two electrochemically analyze samples which may contain a variety of electroactive substances of interest in which there are known or suspected interferring substances, it is a simple matter to store the signal information from each electrode segment and to select out or sort only those active electrode segments which are at the particular electrical potentials which produce the desired electrochemical reactions, derive signals from those electrochemical reactions, and sum (add or subtract) the signals to arrive at the desired measurement. The selected active electrode segments may be connected in manually by the operator, e.g. according to printed instructions. Obviously, such an apparatus may also include a plurality of reagents, supplies, reagent valves, etc. so that a particular reagent may be introduced depending on the particular substance being detected and measured.

The foregoing apparatus has been described as being run under operator control; however, the apparatus can be made to operate automatically as follows: Referring to FIG. 6, a control synchronizer 85 is provided for actuating a pump and valve timing control 86 and also an analog timing control 87. The analog timing control 87 is in the ready position and is activated for analysis by a start analysis control 88 which appears on the apparatus as start test button 24.

Optical sensor 68 whose operation is illustrated in FIG. 5 directs a signal to flow sense circuit 19 which in turn sends a signal to pump and valve timing control 86 and analog timing control 87. Should the flow through line 65 be inadequate for complete flushing of cell 27, the signal from flow sense circuit 90 operates to turn off pump 60 or close valve 63 or both, and to inactivate analog timer control 87 so that an analysis cannot be started without resetting the apparatus.

A power supply 91 operated from an A/C power source 92 supplies a voltage through line 93, a negative voltage through line 94, and a ground potential through line 95 which are supplied to the cell potential control 70. The cell potential control 70 can be controlled by potential set 96.

In a preferred form of automatic controls the apparatus consists of two sections; analog circuitry for converting, conditioning and displaying electrochemical signals; and reagent handling circuitry for automatic sample handling.

The analysis cycle is controlled by two sequential timers 87. The first timing interval (30 seconds) is initiated after the start analysis switch 88 is depressed. This sequence is used to bring the cell to equilibrium. The second interval (20 seconds) is the concentration measurement. During this time the electrochemical signal is converted and displayed. In a preferred form the apparatus displays the "count down" or "count up" digitally during the measurment. Cell reference potential is controlled by potentiastat circuit 70 and is set by control 96. This potential is applied between the reference electrode segment 45 and active electrode segment 42. A difference potential is seen between active electrode segment 43 and reference electrode segment 45. This difference potential is set by offset 2 control operating on current convertor subtractor 75. The equivalent potential becomes $[E_{set\ 1} - E_{offset}]$.

During the measurement inverval the cell currents are fed into current-to-voltage converter circuit 75 and gained controlled by potentiometers "Gain 1" and "Gain 2". The difference of the resulting voltages is taken and fed into the accumulator circuit 76 and integrated during the measurement interval. The integrated voltage then has the "autoblank" value subtracted from it and gained by calibrate circuitry 77.

The resultant value is then displayed on the readout 80 in direct units of micrograms of iron per 100 ml ($\mu$g %) of serum. When the digital display stops counting the reagent or electrolyte containing the sample is flushed into container 28 and a new supply of reagent or electrolyte is introduced into the cell from container 29. When the start test indicator 24 lights up again, the apparatus is ready for a next sample. The entire test may take less than one minute, the largest portion of which is the preliminary mixing time.

Reagent or electrolyte can be automatically charged to the cell in a number of ways. One way is to automatically fill the cell when the unit switches from the standby to run position; another way is to automatically fill the cell at the end of each analysis cycle.

Pump and valve timers are set "on" by the control synchronizer 85 from a trigger signal received by the standby control switch 9or the analysis cycle timer. The solenoid valve 63 is used to control reagent flow into the cell. A pump supplies nominal pressure (e.g. 4 psi) to reagent supply 62 and a nominal e.g. vacuum (17" Hg) to drain reservoir 69. The pressure forces clean reagent through the valve into cell 27. This increase in cell volume is taken off through the drain line to the drain reservoir 69. The reagent inlet valve is timed on for a short time, e.g. 8 seconds, and the pump is left on for an additional 2 seconds to drain any excess reagent above a set level from the cell.

A flow sensor 68 consisting of optical sensor 56 and flow sense circuit 90 monitors the cell drain line 65 during the reagent flushing cycle. If there is no reagent flow or if a low amount of reagent passes through the cell, the flow sense circuit 90 will reset the pump and valve timers and thus prevent the start of an analysis. An audio alarm and indicator light (light 23) may also be activated at this time. Thus, a new cycle cannot be started until the operator places the instrument in the standby condition which resets the flow sense circuit 90.

The flow sense circuit 90 comprises an optical sensor (LED 55 and phototransistor assembly 56, FIG. 5) and is placed at the cell drain line. In operation, the output from flow sense circuit 90 changes from a low voltage (line empty) to a higher voltage level (reagent flowing). This level change is sensed and integrated during the first 4 seconds of the reagent cycle. If the integrator voltage is below a preset level at the end of the 4 second interval, instrument lockout is activated.

In the autoblanking operation, when a blank concentration reading is taken and is to be nulled out of future readings, the unit is switched from "run" to "autoblank". The autoblank set switch is depressed, starting a 4 second timer. The binary coded decimal output from the display is latched in the circuit. This BCD number is then converted from a digital to an analog signal.

An analog voltage of correct polarity and magnitude is fed to the calibration circuitry and subtracted from the concentration analog voltage resulting in a zero output to the display.

Figure 7:
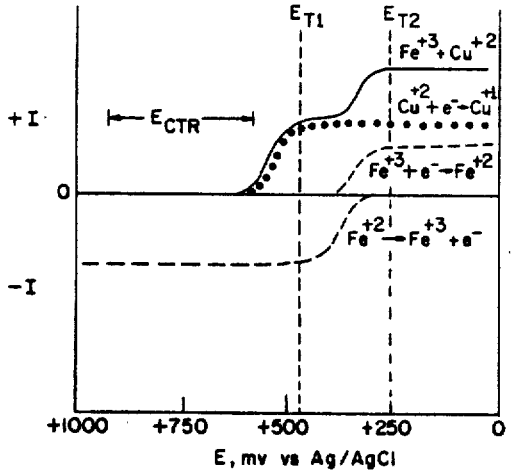
FIG. 7 is a plot showing the current in microamperes, $\mu$A, verses the potential in volts verses a standard silver/silver halide reference electrode, obtained in accordance with the present invention.

Alternatively, the apparatus may be made to operate automatically, e.g. by means of switching using a microprocessor. In such case, for a known substance, a tape containing instrument instructions would be inserted in the microprocessor, which then selects the reagent to be added to the cell, and the electrode potentials. The results could then be displayed for usual observation as on a CRT tube or printed out, or the result, may be read into memory for appropriate mathematical manipulation and then displayed. For an unknown substance, the instrument could be instructed to connect a plurality of electrically discrete active testing electrodes at different electrical potentials to thus reproduce an entire current voltage curve which can then be compared to current voltage curves for known electroactive species. The identification of the unknown species can be determined by matching curve shapes while the amount of an electroactive species present in the sample can be determined from the area under various sections of the curve for the unknown. More specifically, FIG. 7 illustrates a typical current versus potential chart obtained in accordance with this invention. In this graph, the horizontal axis indicates the difference potential, in volts, of working electrodes at increasingly more positive potentials with respect to the silver/silver chloride reference electrode. The vertical axis represents the anodic current, in microamperes, at the indicated potential. The waves of the current versus potential curves indicate a sharp change in current due to the change in concentration of each electroactive species as it reacts in the reagent. Since the potential at which a particular electroactive species reacts is characteristic of a particular species in a particular reagent, the electroactive species present in the sample are readily identified. Also, since the presence of any interferring electroactive species is cancelled out by the electronics, the areas under the peaks are directly related to the total amount of and thus to the concentration of each electroactive species in the sample solution.

A feature and advantage of the present invention is that electrochemical measurements are made of charge transfer reactions substantially simultaneously with the occurrance of the reactions. Thus electrochemical measurements in accordance with the present invention can be carried out simultaneously on more than one substance of interest in a sample by application of suitable electrical potentials on the various active electrode segments; and through signal sorting. For example, a blood sample may be tested simultaneously for lead and chromium.

Various other changes will be obvious to one skilled in the art. For example, the active electrode segments have been illustrated as comprising continuous rings or bands; however, one skilled in the art will recognize that the active electrode segments may comprise individual dots or segments, or a series of dots or segments. Moreover, while the electrode preferably comprises a hollow cylindrical, the similar advantages may be achieved by shaping the electrode as a hollow cone and by providing a stirrer of mating size and shape. Furthermore, one or more active electrode segments may be added to change the electrode area at selected voltage potentials so as to reduce or null out otherwise very large signals from interferring electroactive species, or reagent signals in the case of very dilute solutions, and thus increase sensitivity to a particular electrochemical species of interest, and to balance signals. Moreover, neither the reference electrode nor the counter or power electrode need be mounted as segments or electrode 34, but can be separately provided in known manner in contact with the solution being measured. For example, the reference electrode and/or the counter electrode may be formed in plug 46. Also, the apparatus may comprise more than one reference electrode and/or more than one counter electrode. The apparatus could also be adapted to operate as a flow cell to thus provide a continuous profile of a process.

Figure 8:
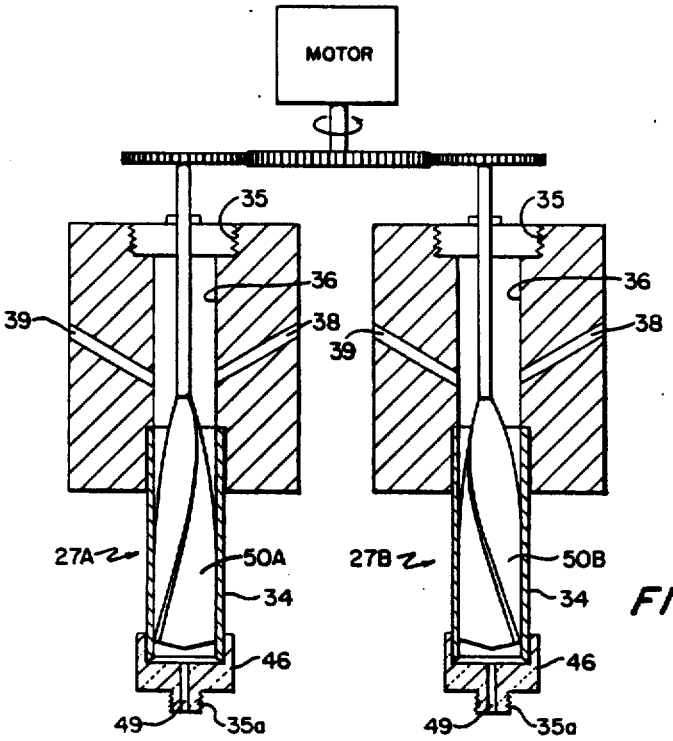
FIGS. 8 and 9 are front views, in perspective, of alternative forms of electrolytic cells in accordance with the present invention.

In addition to the foregoing, it will be understood, as shown in FIG. 8, that the electrochemical system may comprise a pair of side-by-side cell assemblies 27A and 27B. Cell assemblies 27A and 27B are similar to cell assembly 27 as above described. In this latter case one of the cell assemblies, e.g. assembly 27A is designed to be the analysis cell while the other cell assembly 27B is a blank correction cell. Each active electrode segment in cell assembly 27A is paired with a corresponding active electrode segment in cell assembly 27B at the same potential. In use sample containing reagent is injected into cell assembly 27A while pure reagent is injected into cell assembly 27B. The cell contents are stirred at substantially identical rates, and charge transfer signals derived as before. The signals from the active cell segments in the two cell assemblies 27A and 27B are summed, e.g. as by subtracting the signals derived from cell assembly 27B from the signals derived from cell assembly 27A, with the result that all background signals are essentially nulled. An advantage of employing two similar cell assemblies is that signals resulting from impurities in the reagents are nulled. Also, settling effects resulting from a change of reagent, cleaning cycles, etc., are also nulled. Cell assemblies 27A and 27B may comprise identical active electrode areas, or one of the cell assemblies, (typically the blank correction cell assembly 27B) may be made smaller than the analysis cell assembly 27A and the differences in active electrode areas compensated electrically in known manner. As mentioned above, the stirring rate in cell assembly 27A should be substantially identical to the stirring rate in cell assembly 27B. The simplest way to assure matching is to mechanically connect the stirring means 50A and 50B in the two cell assemblies 27A and 27B to a single motor.

Figure 9:
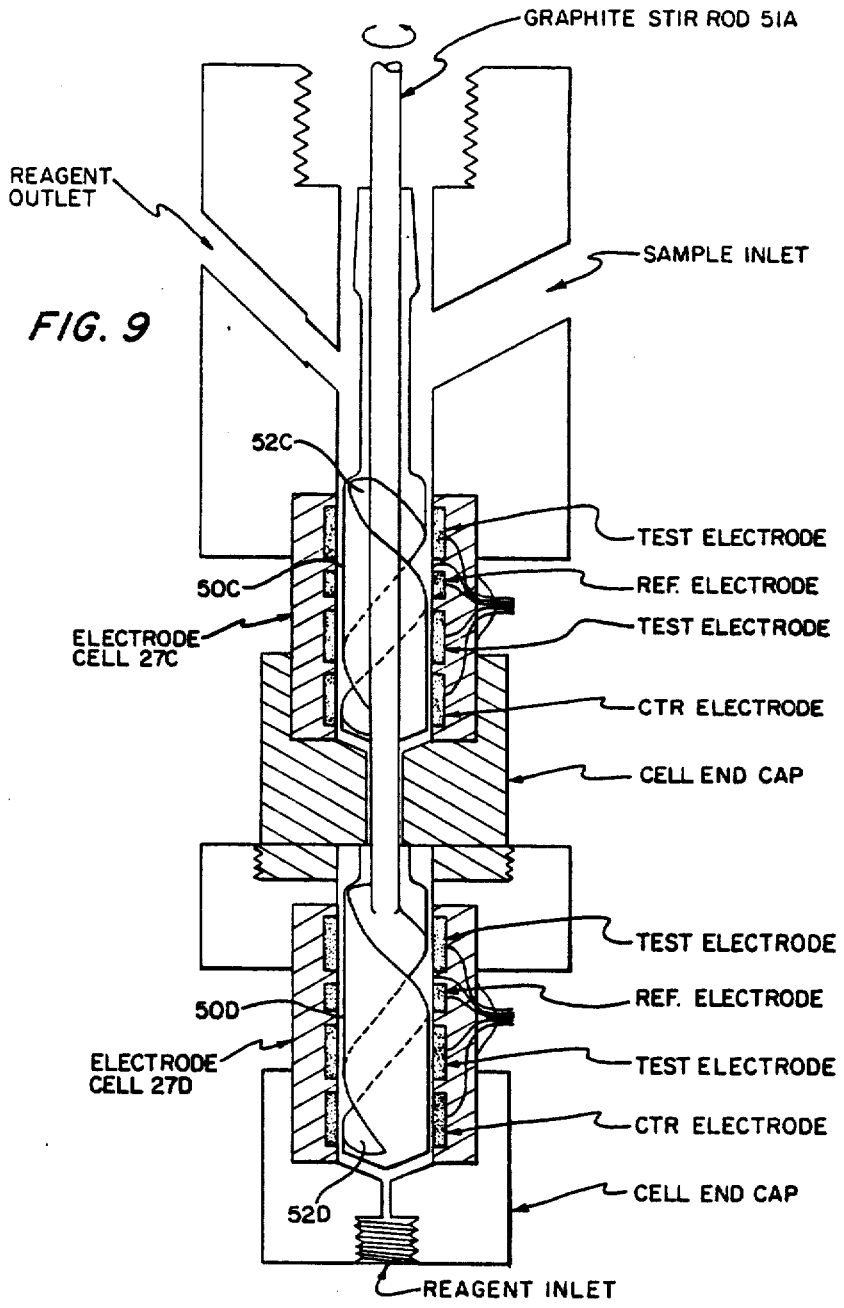

Alternatively, the two cell assemblies may be stacked one on top of another, e.g. as shown in FIG. 9 at 27C and 27D, and the cell contents stirred by a stirring means 50C and 50D which are mounted on a common shaft 51A. Obviously, care must be taken to prevent fluid transport between the two cell assemblies 27C and 27D. This can be assured by close manufacturing tolerances and with sealing means as are well known to one skilled in the art. As before, grooves 52C and 52D are provided on stirring means 50C and 50D, respectively. If desired, these grooves may be made to run in opposite directions to one another to minimize fluid transport between cell 27C and 27D.

A particular feature and advantage of the present invention which results from the use of an electrode having a plurality of active testing electrodes at different potentials in accordance with the preset invention is the elimination of capacitance signals which were inherent in prior art electrochemical measuring in which the potential on an electrode is changed to obtain a measurement.

Still other features, advantages and objects will be obvious to one skilled in the art.

We claim:

1. In serum iron testing, a method of electrochemical testing compatible with micro sized samples of serum comprising:

preparing a substantially iron-free matrix including a lower aliphatic alcohol and between about 5½ Formal and about 8½ Formal HCl;

introducing a predetermined quantity of serum into said matrix to provide an electrolytic sample, and adding a measured quantity of said sample containing a measured quantity of serum to an electrolytic cell;

applying to a first electrode in said cell a potential to measure the quantity of copper and iron in said cell;

applying to a second electrode in said cell a potential to measure a different quantity selected from copper and iron;

obtaining signals corresponding to current flow at each of said electrodes; and comparing said signals to measure the quantity of iron.

2. The method of claim 1, wherein the potential applied to said first electrode is between about 0.4 and about 0.5 volts and the potential applied to said second electrode is between about 0.2 and about 0.3 volts.

3. The method of claim 2, wherein the second electrode signal is subtracted from the first electrode signal.

4. A composition for releasing iron from serum for electrochemical testing comprising a substantially iron-free mixture of a lower aliphatic alcohol, and HCl between about 5½ Formal and about 8½ Formal.

5. A composition according to claim 4, wherein said alcohol comprises isopropanol.

6. A composition according to claim 5, wherein said HCl concentration is about 7 Formal.

[7. Apparatus for electrochemical testing of serum iron comprising:

(a) support means;

(b) a cell block positioned on said support means and including an electrolytic cell to contain a quantity of a sample serum;

(c) an electrode body in said cell having a plurality of electrically discrete active testing electrode segments and at least one reference electrode segment, at least a first said active testing electrode segment being adapted to detect and measure a first quantity corresponding to both iron and copper, and at least a second active testing electrode segment being adapted to detect and measure a different quantity selected from iron and copper, whereby the quantity of iron can be determined by comparing the electrochemical measures of said electrode segments;

(d) means to apply to said first active testing electrode segment a potential for measuring both iron and copper from serum;

(e) means to apply to said second active testing electrode segment a potential for measuring a different quantity selected from iron and copper;

(f) means to compare signals corresponding to electric currents to said first and second active testing electrode segments to determine, by said comparison, the quantity of iron in said sample.]

[8. The apparatus of claim 7, wherein said means to apply a potential to said first active testing electrode segment is operative over a range from zero to 1 volt, and wherein said means to apply a potential to said second active testing electrode segment is operative with respect to said first electrode over a range between zero and 300 millivolts.]

[9. The apparatus of claim 7, wherein said means to apply a potential to said first active testing electrode segment is operative between about 0.4 and about 0.5 volts, and said means to apply a potential to said second active testing electrode is operative between about 0.2 and about 0.3 volts.]

[10. The apparatus of claim 9, wherein said means to apply a potential to said first active testing electrode is operative at about 460 millivolts, and said means to apply a potential to said second active testing electrode is operative at about 250 millivolts.]

11. Apparatus for electrochemical testing of serum iron comprising:

(a) support means;

(b) a cell block positioned on said support means and including an electrolytic cell to contain a quantity of a sample of serum;

(c) an electrode body in said cell having a plurality of electrically discrete active electrode segments and at least one reference electrode segment, at least a first of said active testing electrode segments being adapted to detect and measure both iron and copper, and at least a second of said active testing electrode segments being adapted to detect and measure a different quantity selected from iron and copper, whereby the quantity of iron can be determined by comparing the electrochemical measures of said active testing electrode segments;

(d) stirring means in said cell;

(c) sample input means to receive a measured quantity of a serum sample for testing;

(f) input means to introduce electrolyte liquid to said cell;

(g) outlet means to discharge electrolyte from said cell;

(h) means to supply electrolyte liquid to said cell and to discharge electrolyte through said outlet means;

(i) means to apply to said first active testing electrode segment a potential for measuring both iron and copper from serum;

(j) means to apply to said second active testing electrode segment a potential for measuring a different quantity selected from iron and copper; and (k) means to compare signals corresponding to electric currents to said first and second active testing electrodes to determine, by said comparison, the quantity of iron in said sample.

[12. In apparatus according to claim 11, means to flush electrolyte through said cell to remove electrolyte therefrom and to replace it with fresh electrolyte, said means comprising conduit means to supply electrolyte to said input, conduit means to receive electrolyte from said outlet, an optical emitter and an optical detector on opposite sides of one of said conduit means, and curved transparent walls in said conduit between said emitter and said detector, whereby radiation from said emitter is more fully focused on said detector while electrolyte liquid is in said conduit.]

[13. Apparatus for electrochemical testing of serum iron comprising;

(a) support means;

(b) a cell block positioned on said support means and including an electrolytic cell to contain a quantity of a sample of serum;

(c) an electrode body in said cell having a plurality of electrically discrete active electrode segments and at least one reference electrode segment, at least a first of said active testing electrode segments being adapted to measure a first charge transfer for both iron and copper, and at least a second of said active testing electrode segments being adapted to measure a second charge transfer for a different quantity selected from iron and copper, whereby the quantity of iron can be determined by comparing the measures of said charge transfers;

(d) means to apply to said first active testing electrode segment a first potential for measuring the charge transfer of both iron and copper;

(e) means to apply to said second active testing electrode segment a second potential for measuring the charge transfer of a different quantity selected from iron and copper;

(f) means to compare signals corresponding to first and second charge transfers to determine, by said comparison, the quantity of iron in said sample.]

[14. The apparatus according to claim 13, including means for subtracting a signal corresponding to said second charge transfer from a signal corresponding to said first charge transfer.]

[15. The apparatus of claim 13, wherein said means to apply said first potential is operative at about 460 millivolts, and said means to apply said second potential is operative about 250 millivolts.]

[16. Apparatus according to claim 7, including means to flush from said cell electrolyte containing a sample and to replace it with new electrolyte.]

[17. Apparatus according to claim 15, including digital display means for displaying the result obtained by subtracting said second signal from said first signal.]

[18. Apparatus according to claim 17 including calibration means for converting said display to a digital readout of micrograms of iron per 100 milliliters of serum.]

19. The method of claim 3, and including the step of converting the result of said signal subtraction to a digital display.

[20. An electrode for electrochemical testing adapted to measure simultaneously at least two electrolytic potentials with reference to a reference potential comprising:

a hollow cylindrical electrode body of an insulating material, open at least at one end;

a smooth cylindrical inner surface on said electrode body;

at least one reference electrode segment and at least two active testing electrode segments mounted at the inner surface of said electrode body and having their respective surfaces flush with the inner surface of said body, each of said segments being electrically insulated from each other electrode segment and separated therefrom by said insulating material;

said reference electrode segment having at least its surface formed of a reference metal; and means to connect each of said active testing electrode segments to a different electrical potential.]

[21. An electrode according to claim 20, having first, second, third and fourth electrode segments;

said first and second segments being active testing electrode segments adapted to measure simultaneously two electrolytic potentials;

said third segment being a reference electrode segment; and said fourth segment being adapted to provide an electrolytic current source different from the potentials on said first, second and third electrode segments.]

[22. The electrode of claim 21, wherein said reference electrode segment comprises silver and said first, second and fourth electrode segments each comprise carbon.]

23. In serum iron testing by electrochemical methods, the steps of:

preparing a substantially iron free matrix comprising between 5½ and 8½ Formal HCl in isopropanol;

adding to said matrix a measured quantity of a serum sample to be tested, thereby releasing serum iron from binding to serum components, *impressing a first potential for measuring the charge transfer of iron and copper and deriving a signal therefrom; impressing a second potential for measuring the charge*

*transfer of a different quantity selected from iron and copper and deriving a signal therefrom;* and separating the charge transfer potentials of iron and copper *by simultaneously measuring the charge transfers at said two different potentials;* and thereafter [measuring] *comparing said signals whereby to determine* the quantity of electrolytic current corresponding to iron charge transfer in said sample *by comparing said measured charge transfers.*

[24. An electroytic cell for electrochemically testing a sample in solution, said cell comprising:

a sensing electrode in the form of a hollow cylindrical body defining an enclosure for holding said solution for testing, said body (a) being formed of an electrically insulating material, and (b) having a substantially smooth cylindrical inner surface;

at least two active testing electrode segments mounted at the inner surface of said body, said electrode segments having electrically active surfaces which are (a) substantially flush with said smooth inner surface, and (b) electrically insulated from one another by said insulating material;

a counter electrode having an electrically active surface mounted in said enclosure;

a reference electrode having an electrically active surface mounted in said enclosure; and means for connecting (a) said at least two active testing segments to different electrical potential, (b) said reference electrode to a reference potentials, and (c) said counter electrode to yet another potentials.]

[25. An electrolytic cell according to claim 24 wherein said reference electrode comprises one or more electrode segments mounted at the inner surface of said body, each of said reference electrode segments having an electrically active surface which is (a) substantially flush with the inner surface of said body, and (b) electrically insulated from all other electrode segments on said body.]

[26. An electrolytic cell according to claim 24 wherein said counter electrode comprises one or more electrode segments mounted at the inner surface of said body, each of said counter electrode segments having an electrically active surface which is (a) substantially flush with the inner surface of said body, and (b) being electrically insulated from all other electrode segments on said body.]

[27. An electrode according to claim 24 wherein said reference electrode comprises silver.]

[28. An electrode according to any one of claims 24 to 26 wherein said reference electrode comprises silver, and said active testing electrodes and said counter electrode comprise carbon.]

[29. An electrolytic cell assembly comprising first and second electrolytic cells as defined by claim 24, said first electrolytic cell being adapted to hold a sample in a reagent and to measure charge transfer reactions of said sample and said reagent, said second electrolytic cell being adapted to hold said reagent alone and to measure charge transfer reactions of said reagent alone, said first and said second electrolytic cells having corresponding active electrode segments, and means for pairing electrode segments in said first electrolytic cell with corresponding electrode segments in said second electrolytic cell at the same potential.]

[30. In a method of electrochemically analyzing a sample material to identify selected substances therein, the steps of: dissolving said sample in a reagent to form a test solution, charging a quantity of said test solution to an electrolytic cell in contact with a plurality of active testing electrodes, simultaneously providing a plurality of electrical potentials across said solution from said plurality of active testing electrodes, deriving signals from said active testing electrodes corresponding to charge transfer reactions of materials in said solution, and sorting said signals to obtain signals which identify said selected substances.]

[31. Apparatus for electrochemical testing a sample in solution to identify selected substances therein, said apparatus comprising at least one electrolytic cell as defined by claim 24, and further comprising means for comparing signals corresponding to electric current flow at at least two active testing segments to determine, by said comparison, the quantity of said selected substances in said sample.]

32. Apparatus [according to claim 31, including] *for electrochemical testing a sample in solution to identify selected substances therein, said apparatus comprising at least one electrolytic cell comprising:*

*a sensing electrode in the form of a hollow cylindrical body defining an enclosure for holding said solution for testing, said body (a) being formed of an electrically insulating material, and (b) having a substantially smooth cylindrical inner surface;*

*at least two active testing electrode segments mounted at the inner surface of said body, said electrode segments having electrically active surfaces which are (a) substantially flush with said smooth inner surface, and (b) electrically insulated from one another by said insulating material;*

*a counter electrode having an electrically active surface mounted in said enclosure;*

*a reference electrode having an electrically active surface mounted in said enclosure;*

*means for connecting (a) said at least two active testing segments to different electrical potentials, (b) said reference electrode to a reference potential, and (c) said counter electrode to yet another potential, said cell being arranged so that the concentration of each ion species is essentially identical at each testing electrode; and,*

*means for comparing signals corresponding to charge transfer reactions simultaneously obtained from each of said active testing electrodes, and means for comparing signals corresponding to electric current flow at at least two active testing segments to determine, by said comparison, the quantity of said selected substances in said sample; said apparatus further including:*

(a) stirring means mounted in said sensing electrode;

(b) sample input means for introducing a measured quantity of sample into said sensing electrode;

(c) input means for introducing electrolyte liquid to said sensing electrode;

(d) outlet means for discharging electrolyte from said sensing electrode; and (e) means for supplying electrolyte to said input means.

33. Apparatus according to [claims 31 or] *claim* 32 for electrochemical testing a sample selected from the group consisting of blood and serum, containing both iron and copper, wherein one of said active electrode segments is adapted to measure a first charge transfer for both iron and copper, and another of said active electrode segments is adapted to measure a second charge transfer for a different quantity selected from iron and copper, and including means for applying to said one active electrode segment a first potential for measuring the charge transfer of both iron and copper; means for applying to said another active electrode segment a second potential for measuring the charge transfer of said different quantity selected from iron and copper; and means for comparing signals corresponding to first and second charge transfers to determine, by said comparison, the quantity of iron in said sample.

34. Apparatus according to [claims 31 or] *claim* 32, and including means for flushing electrolyte through said cell to remove electrolyte therefrom and to replace it with fresh electrolyte, [said] *a* means for flushing comprising *first and second conduits,* a first conduit for receiving spent electrolyte from said cell, an optical emitter and an optical detector on opposite sides of one of said first and second conduits, and curved transparent walls in said one of said conduits between said emitter and said detector, whereby radiation from said emitter is more fully focussed on said detector while electrolyte liquid is in said conduit.

[35. In a method according to claim 30, the step of applying a potential of between about zero and 1 volt to one of said active testing electrodes, and a potential of between about zero and 300 millivolts to another of said active testing electrodes.]

[36. In a method according to claim 30, wherein said sample is suspected of containing a metal selected from the group consisting of molybdenum tungsten, titanium, vanadium, and uranium, the improvement wherein said reagent comprises an alcoholic HCl solution.]

[37. In a method according to claim 30, wherein said sample is suspected of containing chromium, the improvement wherein said reagent comprises an alcoholic hydroxide solution.]

[38. In a method according to claim 30, wherein said sample is selected from the group consisting of blood and serum and contains both iron and copper, the improvement wherein said reagent comprises a substantially iron-free misture of a lower aliphatic alcohol, and HCl between about 5½ and 8½ Formal.]

39. In a method according to claim [38] *54*, including the steps of introducing a predetermined quantity of said sample into said mixture to form said test solution, and adding a measured quantity of said test solution to an electrolytic cell;

applying to a first active testing electrode in said cell a potential to measure the quantity of copper and iron in said cell;

applying to a second active testing electrode in said cell a potential to measure a different quantity selected from copper and iron;

obtaining signals corresponding to current flow at each of said first and second active testing electrodes; and comparing said signals to measure the quantity of iron.

40. In a method according to claim 39, wherein a potential of between about 0.4 and 0.5 volts is applied to said first active testing electrode, a potential of between about 0.2 and 0.3 volts is applied to said second active testing electrode; and the signal from said second active testing electrode is subtracted from the signal from said first active testing electrode.

41. In a method according to claim 40, wherein said potential applied to said first active testing electrode is about 460 millivolts and the potential applied to said second active testing electrode is about 250 millivolts.

42. In a method according to claim [38] *54*, wherein said alcohol comprises isopropanol.

43. In a method according to claim [38] *54*, wherein said HCl concentration is about 7 Formal.

44. A composition according to claim 4, and including a minute quantity of silver [iron] *ion.*

*45. The method of electrochemically analyzing the concentration of a first ion species in a sample which also contains a second ion species comprising the steps of dissolving said sample in a reagent to form a reagent containing said test solution, charging a quantity of said reagent containing said test solution to an electrolytic cell in contact with a plurality of active testing electrodes, applying to a first active testing electrode segment a first potential for measuring the charge transfer of both said ion species, applying to a second active testing electrode segment a second potential for simultaneously measuring the charge transfer of a different quantity selected from one of said ion species while maintaining essentially the same concentration of ion species at both electrodes, said first active testing electrode segment and said second active testing segment being arranged to measure charge transfers on said reagent containing said test solution having essentially the same ion concentration in solution at both said electrode segments; and comparing signals corresponding to first and second charge transfers to determine, by said comparison, the quantity of said first species in said sample.*

*46. The process of claim 45 which also includes the electrochemical measuring of the concentration of a second ion species in the presence of a third ion species comprising the additional steps of applying to a third active testing electrode segment a third potential for simultaneously measuring the charge transfer of a third quantity selected from one or more of said ion species,*

*and comparing signals corresponding to first, second and third charge transfers to determine, by said comparison, the quantity of said first and second species in said sample.*

*47. The process of claim 45 which includes the additional steps of using a pair of electrolytic cells, charging to one of said cells said sample-reagent mixture and to the other of said cells reagent free of said sample, applying equivalent potentials to first and second active testing electrodes in said second cell which are equivalent to the potentials applied to the equivalent electrodes in the first cell, and pairing electrodes in said first electrolytic cell with corresponding electrode segments in said second electrolytic cell so as to null background signals due to charge transfer measurements of the reagent and its impurities.*

*48. Apparatus for electrochemical measuring of the concentration of a first ion species in a sample dissolved in a reagent which also contains a second ion species comprising:*

*(a) a support arm;*

*(b) a cell block positioned on said support means and including an electrolytic cell to contain a quantity of reagent containing both said ion species;*

*(c) an electrode body in said cell having a plurality of electrically discrete active testing electrode segments and at least one reference electrode segment, at least a first of said active testing electrode segments being adapted to measure a first charge transfer for both said ion species and at least a second of said active testing electrode segments being adapted to simultaneously measure a second charge transfer for a different quantity selected from one of said ion species, said*

*test electrodes being arranged to measure charge transfers on a reagent containing said test solution having essentially the same ion concentration in solution of both test electrodes, whereby the quantity of said first species can be determined by comparing the measures of said charge transfers;*

*(d) means to apply to said first active testing electrode segment a first predetermined potential for measuring the charge transfer of both said ion species;*

*(e) means to apply to said second active testing electrode segment a second predetermined potential for simultaneously measuring the charge transfer of a different quantity selected from one of said ion species;*

*(f) means to compare signals corresponding to first and second charge transfers to determine, by said comparison, the quantity of said first species in said sample; and*

*(g) means for stirring the reagent adjacent the electrode segments during measurement.*

*49. An electrode system, for electrochemical testing of a solution containing several ion species and adapted to measure simultaneously at least two electrolytic potentials with reference to a reference potential comprising:*

*a hollow cylindrical electrode body of an insulating material, open at least at one end;*

*a smooth cylindrical inner surface on said electrode body;*

*at least one reference electrode segment and at least two active testing electrode segments mounted at the inner surface of said electrode body and having their respective surfaces flush with the inner surface of said body, each of said segments being electrically insulated from each other electrode segment and separated therefrom by said insulating material;*

*said reference electrode segment having at least its surface formed of a reference metal;*

*means to connect each of said active testing electrode segments to a different electrical potential, said electrode system being arranged so that the concentration of each ion species is essentially identical at each testing electrode;*

*means for generating signals corresponding to charge transfer reactions simultaneously obtained from each of said active testing electrodes and for comparing said generated signals; and*

*stirring means for continuously mixing the solution so that the concentration of each ion species is essentially identical at each testing electrode.*

*50. An electrolytic cell for electrochemically testing a sample containing several ion species in solution, said cell comprising:*

*a sensing electrode in the form of a hollow cylindrical body defining an enclosure for holding said solution for testing, said body (a) being formed of an electrically insulating material, and (b) having a substantially smooth cylindrical inner surface;*

*at least two active testing electrode segments mounted at the inner surface of said body, said electrode segments having electrically active surfaces which are (a) substantially flush with said smooth inner surface, and (b) electrically insulated from one another by said insulating material;*

*a counter electrode having an electrically active surface mounted in said enclosure;*

*a reference electrode having an electrically active surface mounted in said enclosure;*

*means for connecting (a) said at least two active testing segments to different electrical potentials, (a) said reference electrode to a reference potential, and (c) said counter electrode to yet another potential, said cell being arranged so that the concentration of each ion species is essentially identical at each testing electrode;*

*means for comparing signals corresponding to charge transfer reactions simultaneously obtained from each of said active testing electrodes; and*

*stirring means for continuously mixing the solution so that the concentration of each ion species is essentially identical at each testing electrode.*

*51. Apparatus for electrochemical testing of serum iron comprising:*

*(a) support means;*

*(b) a cell block positioned on said support means and including an electrolytic cell to contain a quantity of a sample of serum;*

*(c) an electrode body in said cell having a plurality of electrically discrete active electrode segments and at least one reference electrode segment, at least a first of said active testing electrode segments being adapted to detect and measure both iron and copper, and at least a second of said active testing electrode segments being adapted to detect and measure a different quantity selected from iron and copper, whereby the quantity of iron can be determined by comparing the electrochemical measures of said active testing electrode segments;*

*(d) stirring means in said cell;*

*(e) sample input means to receive a measured quantity of a serum sample for testing;*

*(f) input means to introduce electrolyte liquid to said cell;*

*(g) outlet means to discharge electrolyte from said cell;*

*(h) means to supply electrolyte to said cell and to remove electrolyte therefrom and to replace it with fresh electrolyte, said means comprising conduit means to supply electrolyte to said input, conduit means to receive electrolyte from said outlet, an optical emitter and an optical detector on opposite sides of one of said conduit means and curved transparent walls in said conduit between said emitter and said detector, whereby radiation from said emitter is more fully focussed on said detector while electrolyte liquid is in said conduit;*

*(i) means to apply to said first active testing electrode segment a potential for measuring both iron and copper from serum;*

*(j) means to apply to said second active testing electrode segment a potential for measuring a different quantity selected from iron and copper; and*

*(k) means to compare signals corresponding to electric currents to said first and second active testing electrodes to determine, by said comparison, the quantity of iron in said sample.*

*52. In a method of electrochemically analyzing a sample material to identify selected substances therein, wherein said sample is suspected of containing a metal selected from the group consisting of molybdenum, tungsten, titanium, vanadium and uranium, the improvement which comprises dissolving said sample in a reagent comprising an alcoholic HCl solution to form a test solution, charging a quantity of said test solution to an electrolyte cell where said test solution is in contact with a plurality of different electrical potentials across said solution from a plurality of active testing electrodes, deriving signals from said active testing electrodes corresponding to charge transfer reactions of materials in said solution, and sorting said signals to obtain signals which identify said selected substances.*

*53. In a method of electrochemically analyzing a sample material to identify selected substances therein, wherein said sample is suspected of containing chromium, the improvement which comprises dissolving said sample in a reagent comprising an alcoholic hydroxide solution to form a test solution, charging a quantity of said test solution to an electrolytic cell in contact with a plurality of active testing electrodes, simultaneously providing a plurality of different electrical potentials across said solution from a plurality of active testing electrodes, deriving signals from said active testing electrodes corresponding to charge transfer reactions of materials in said solution, and sorting said signals to obtain signals which identify said selected substances.*

*54. In a method of electrochemically analyzing a sample material to identify selected substances therein, wherein said sample is selected from the group consisting of blood and serum and contains both iron and copper, the improvement which comprises dissolving said sample in a reagent comprising a substantially iron-free mixture of a lower aliphatic alcohol, and HCl between about 5½ Formal and 8½ Formal to form a test solution, charging a quantity of said test solution to an electrolytic cell where said test solution is in contact with a plurality of different electrical potentials across said solution from a plurality of active testing electrodes, deriving signals from said active testing electrodes corresponding to charge transfer reactions of materials in said solution, and sorting said signals to obtain signals which identify said selected substances.*

* * * * *